(12) United States Patent
Beghetto

(10) Patent No.: US 12,215,088 B2
(45) Date of Patent: Feb. 4, 2025

(54) METHOD FOR THE INDUSTRIAL PRODUCTION OF 2-HALO-4,6-DIALKOXY-1,3,5-TRIAZINES AND THEIR USE IN THE PRESENCE OF AMINES

(71) Applicant: CROSSING SRL, Treviso (IT)

(72) Inventor: Valentina Beghetto, Mestre (IT)

(73) Assignee: CROSSING SRL, Treviso (IT)

( * ) Notice: Subject to any disclaimer, the term of this patent is extended or adjusted under 35 U.S.C. 154(b) by 549 days.

(21) Appl. No.: 17/382,591

(22) Filed: Jul. 22, 2021

(65) Prior Publication Data

US 2021/0355091 A1 Nov. 18, 2021

Related U.S. Application Data

(62) Division of application No. 15/535,992, filed as application No. PCT/IB2015/059892 on Dec. 22, 2015, now Pat. No. 11,111,221.

(30) Foreign Application Priority Data

Dec. 23, 2014 (IT) .......................... VE2014A000070
Dec. 23, 2014 (IT) .......................... VE2014A000071

(51) Int. Cl.
| | | |
|---|---|---|
| C07B 43/04 | (2006.01) |
| C07B 53/00 | (2006.01) |
| C07D 251/26 | (2006.01) |
| C07D 251/46 | (2006.01) |
| C08J 3/24 | (2006.01) |
| C14C 3/26 | (2006.01) |

(52) U.S. Cl.
CPC ............ *C07D 251/26* (2013.01); *C07B 43/04* (2013.01); *C07B 53/00* (2013.01); *C07D 251/46* (2013.01); *C08J 3/24* (2013.01); *C14C 3/26* (2013.01); *C08J 2301/28* (2013.01); *C08J 2389/00* (2013.01)

(58) Field of Classification Search
CPC ....... C07D 251/26; C07B 43/04; C07B 53/00; C08J 53/00; C08J 3/24; C08J 2301/28; C08J 2389/00; C14C 3/26; C07C 231/02; C07C 233/65

See application file for complete search history.

(56) References Cited

U.S. PATENT DOCUMENTS

| | | |
|---|---|---|
| 4,076,538 A | 2/1978 | Smith |
| 6,458,948 B1 | 10/2002 | Iwasaki et al. |
| 8,119,592 B2 | 2/2012 | Beigelman et al. |
| 8,679,196 B2 | 3/2014 | Reineking et al. |
| 8,691,279 B2 | 4/2014 | Guillen et al. |
| 2002/0123628 A1 | 9/2002 | Saijo et al. |
| 2003/0153785 A1* | 8/2003 | Hirano ................. C07D 501/04 562/512 |
| 2008/0234254 A1 | 9/2008 | Grigg et al. |
| 2011/0118265 A1 | 5/2011 | Stock et al. |
| 2012/0009223 A1 | 1/2012 | Wenguang et al. |
| 2013/0123508 A1 | 5/2013 | Bretonniere et al. |
| 2013/0165533 A1 | 6/2013 | Liao et al. |
| 2013/0219634 A1 | 8/2013 | Reineking et al. |

FOREIGN PATENT DOCUMENTS

| | | | |
|---|---|---|---|
| CN | 101624379 | 1/2010 | |
| CN | 103274962 | 9/2013 | |
| EP | 1 085 000 | 3/2001 | |
| EP | 1 714 962 | 10/2006 | |
| EP | 1 748 985 | 2/2007 | |
| EP | 1 992 364 | 11/2008 | |
| GB | 1311736 | 3/1973 | |
| JP | 2002-20374 | 1/2002 | |
| JP | 2011256219 A | * 12/2011 | ............ C08G 73/22 |
| WO | 2007/051496 | 5/2007 | |
| WO | 2010/056778 | 5/2010 | |
| WO | 2014/063102 | 4/2014 | |

OTHER PUBLICATIONS

English translation of JP-2011256219-A. (Year: 2024).*
International Search Report and Written Opinion of the International Searching Authority issued Aug. 8, 2016 in International (PCT) Application No. PCT/IB2015/059892.
International Preliminary Report on Patentability issued May 8, 2017 in International (PCT) Application No. PCT/IB2015/059892.
Cronin et al., "An Improved Procedure for the Large Scale Preparation of 2-Chloro-4,6-Dimethoxy-1,3,5-Triazine", Synthetic Communications, vol. 26, No. 18, 1996, pp. 3491-3494.

(Continued)

*Primary Examiner* — Amanda L. Aguirre
*Assistant Examiner* — Sagar Patel
(74) *Attorney, Agent, or Firm* — WENDEROTH, LIND & PONACK, L.L.P.

(57) ABSTRACT

A method for stabilization of collagen matrices and of condensation of natural and synthetic polymers that uses 2-halo-4,6-dialkoxy-1,3,5-triazines in the presence of one or more amines as activating agents for reactions of crosslinking, condensation, grafting, and curing of collagen matrices, cellulose, modified celluloses, polysaccharides, acid unsaturated polymers, and chiral and non-chiral amines, etc. Forming an integral part of the present invention is also the method for production on an industrial scale of 2-halo-4,6-dialkoxy-1,3,5-triazines.

12 Claims, 1 Drawing Sheet

(56) References Cited

OTHER PUBLICATIONS

Bowes et al., "Crosslinking of Collagen", Journal of Applied Chemistry, vol. 15, No. 7, Jul. 1965, pp. 296-304, XP002750889.

El-Faham et al., "Peptide Coupling Reagents, More than a Letter Soup", Chemical Reviews, vol. 111, 2011, pp. 6557-6602.

Khor, "Methods for the treatment of collagenous tissues for bioprostheses", Biomaterials, vol. 18, No. 2, 1997, pp. 95-105.

Duan et al., "Dendrimer crosslinked collagen as a corneal tissue engineering scaffold: Mechanical properties and corneal epithelial cell interactions", Biomaterials, vol. 27, May 19, 2006, pp. 4608-4617.

Kamiński et al., "N-Triazinylammonium Tetrafluoroborates. A New Generation of Efficient Coupling Reagents Useful for Peptide Synthesis", J. Am. Chem. Soc., vol. 127, 2005, pp. 16912-16920.

Kunishima et al., "Study on 1,3,5-Triazine Chemistry in Dehydrocondensation: Gauche Effect on the Generation of Active Triazinylammonium Species", Chem. Eur. J., vol. 18, 2012, pp. 15856-15867.

Dudley et al., "Cyanuric Chloride Derivatives. III. Alkoxy-s-triazines", J. Am. Chem. Soc., vol. 73, Jul. 1951, pp. 2986-2990.

Raw, "An improved process for the synthesis of DMTMM-based coupling reagents", Tetrahedron Letters, vol. 50, Dec. 16, 2008, pp. 946-948.

Kunishima et al., "4-(4,6-Dimethoxy-1,3,5-triazin-2-yl)-4-methylmorpholinium Chloride: An Efficient Condensing Agent Leading to the Formation of Amides and Esters", Tetrahedron, vol. 55, 1999, pp. 13159-13170.

Kunishima et al., "Synthesis of Aza-Bridged Calix(4-Methoxy)Triazines Toward Flattened π- Conjugated Macrocycles", Heterocycles, 2009, vol. 79, pp. 609-616.

Kunishima et al., "Study of the Reactivities of Acid-Catalyzed O-Benzylating Reagents Based on Structural Isomers of 1,3,5-Triazine", J. Org. Chem., 2015, vol. 80, pp. 11200-11205.

Tanaka et al., " Novel dialkoxytriazine-type glycosyl donors for cellulase-catalysed lactosylation", Organic Biomol. Chem., 2010, vol. 8, pp. 5126-5132.

Schroeder et al., "Triazines. XIV. The Extension of the Pinner Synthesis of Monohydroxy-s-triazines to the Aliphatic Series. 2,4-Dimethyl-s-triazine[1-3]", C. Journal American Chemical Society, 1956, vol. 78, pp. 2447-2451.

\* cited by examiner

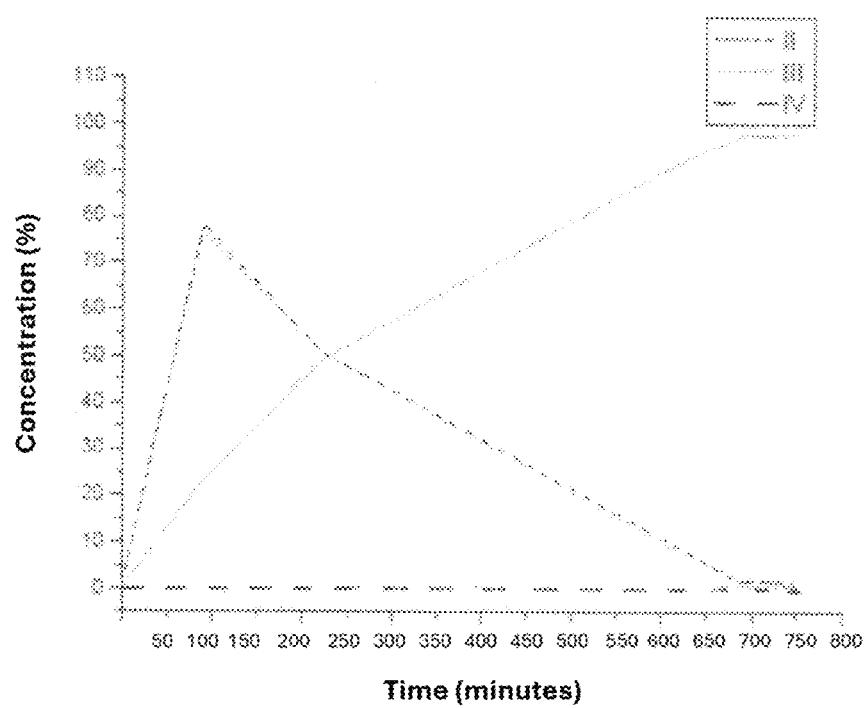

METHOD FOR THE INDUSTRIAL PRODUCTION OF 2-HALO-4,6-DIALKOXY-1,3,5-TRIAZINES AND THEIR USE IN THE PRESENCE OF AMINES

FIELD OF APPLICATION OF THE INVENTION

The present invention relates to the sector of activating agents for condensation, crosslinking, grafting, and curing reactions that intervene in the processes of stabilization of collagen matrices, and for the condensation of natural and synthetic polymers.

In particular, the invention regards the process of synthesis, which can be implemented also on an industrial scale, of 2-halo-4,6-dialkoxy-1,3,5-triazines, which act as activating agents for condensation, crosslinking, grafting, and curing reactions, and for stabilization of collagen matrices, as well as for the condensation of polymers, and the multiple applications of said reagents in various industrial sectors, amongst which the tanning industry and the leather-processing industry.

PRIOR ART

Commonly, amides, esters, and thioesters are formed from the reaction between an amine, alcohol, thioalcohol, and an "activated" carboxylic acid, i.e., obtained by formation of acyl chlorides, mixed anhydrides, or activated esters. These reactions underlie processes for production of a vast range of products in the most disparate sectors, such as those of pharmaceuticals, polymers, packaging, foodstuffs, tissues, etc.

In particular, carbodiimides are organic reagents widely used for the formation of amide bonds, ester bonds, thioester bonds, etc., in so far as they are able to react with carboxylic acids to form an active intermediate species, which, in the presence of an amine, alcohol, or thioalcohol, reacts to form the desired bond [A. El-Faham, Chem. Rev., 2011, 111, 6557-6602]. One of the carbodiimides most frequently used is dicyclohexylcarbodiimide (DCC); however, during the reaction, DCC leads to the formation of a toxic co-product that must be carefully removed at the end of the reaction. Reactions in the presence of carbodiimides are prevalently carried out in organic solvent, since these molecules are not stable in aqueous solution, except for 1-ethyl-3-(3-dimethylaminopropyl)carbodiimide chlorohydrate (EDC). EDC, however, calls for the combined use of equimolar amounts (or higher amounts) of N-hydroxysuccinimide (NHS), which is rather unstable and must be stored at low temperature (approximately −20° C.) and is very expensive. Currently, this reagent is in any case one of the most widely used for the production of polyaminoacids and of other pharmaceutical derivatives with high added value, as well as for crosslinking of collagen, for the reconstruction of tendons and retinas, the production of hydrogels, etc. [U.S. Pat. No. 8,691,279, US 2012/0009223 A1].

In the biotechnology sector, carbodiimides (for example, EDC/NHS) are widely used as alternatives to glutaraldehyde for crosslinking of collagen thanks to their lower toxicity. However, the properties of materials crosslinked with the exclusive use of carbodiimides, the gelatinization temperature (Tg), and the physico-mechanical properties are clearly inferior.

To obtain collagen matrices having characteristics comparable to those obtained with glutaraldehyde, acyl azides, and glycerol [E. Khor, Biomaterials, 1997, 18, 95-105], carbodiimides are normally used in the presence of crosslinking agents that remain permanently attached to the collagen tissue [X. Duan, Biomaterials, 2006, 27, 4608-4615].

It is known that the derivatives of 2-halo-4,6-dialkoxy-1,3,5-triazines, and in particular their quaternary ammonium salts, represent a valid alternative to carbodiimides and can be used, also in an aqueous environment, for the formation of amide bonds, ester bonds, and thioester bonds by means of reactions of crosslinking, grafting, curing, etc. in homogeneous and/or heterogeneous phase [U.S. Pat. No. 6,458,948 B1, Z. J. Kaminski, J. Am. Chem. Soc., 2005, 127, 16912-16920]. In a large number of cases, these reagents are more efficient than other coupling agents known to date, such as DCC, EDC/NHS, PyBOP, HATU, HBTU, etc. An alternative, at present rarely employed, is to resort to the use of the quaternary ammonium salts of 2-halo-4,6-dialkoxy-1,3,5-triazines, and in particular 4-(4,6-dimethoxy-1,3,5-triazin-2-yl)-4-methylmorpholinium chloride (DMTMM) (the only one commercially available), for stabilization of complex matrices for medical use, made up of collagen in combination with other natural and/or synthetic matrices [EP1748985 B1, US 2008/0234254 A1, US 2011/118265 A1, U.S. Pat. No. 8,119,592, WO 2010/056778A].

The quaternary ammonium salts of 2-halo-4,6-dialkoxy-1,3,5-triazines do not present problems of toxicity in the end products since they are not withheld therein and can be easily eliminated at the end of the treatment/reaction. For these reasons, the scientific literature regarding DMTMM has undergone continuous growth in the last few years. For instance, the international patent application No. WO 2014/063102 presents the use of DMTMM for the preparation of artificial lubricants for cartilage. The derivatives of 2-halo-4,6-dialkoxy-1,3,5-triazines are, however, very sensitive to the solvent, and this constitutes a limit to their use. Up to the present day, the literature regarding the synthesis of derivatives of 2-halo-4,6-dialkoxy-1,3,5-triazines is rather limited and in all cases involves at least two steps: 1) synthesis of the triazine derivative from the corresponding 2-halo-4,6-dialkoxy-1,3,5-triazine in the presence of an amine in a given solvent, normally an organic one; 2) recovery and purification of the product before use [U.S. Pat. No. 6,458,948B1; US 2003/0153785A1; EU174962B1/2006; WO2007/051496A1; S. S. A. Raw, Tetrah. Lett., 2009, 50, 946-948]. However, this protocol, which is generally used for the synthesis of organic compounds, also referred to as "Isolated-Product Protocol" (IPP), presents a certain number of critical features, above all from the standpoint of industrial production, in so far as it calls for complex reactors, large amounts of solvents, complicated purification steps, etc., which moreover reduce considerably the yield in the desired product, leading to an increase in the operating costs and hence sales prices.

M. Kunishima et al. have studied the mechanism of reaction of dehydrocondensations in the presence of quaternary ammonium salts of 2-halo-4,6-dialkoxy-1,3,5-triazines [Chem. Eur. J. 2012, 18, 15856-15867]. The authors give some examples of reactions conducted in $CH_2Cl_2$, a solvent in which the quaternary ammonium salts of 2-halo-4,6-dialkoxy-1,3,5-triazines are highly unstable, leading to rapid decomposition. To overcome this problem, the authors present some examples of reactions between a carboxylic acid and a primary amine, in the presence of CDMT and a tertiary amine, but probably on account of the solvent used ($CH_2Cl_2$) and the absence of buffers, auxiliaries, etc., in the majority of cases the main product obtained is the product of condensation between the triazine and the primary amine, instead of the desired amide. Currently, only 2-chloro-4,6-dimethoxy-1,3,5-triazine (CDMT) and 4-(4,6-dimethoxy-1,3,5-triazin-2-yl)-4-methylmorpholinium chloride (DMTMM), are commercially available, at very high prices, on account of the lack of an adequate process on an industrial scale for their production (in terms of kilograms per day or tonnes per day).

In the recent literature, there have been described many examples of application that use DMTMM obtained by means of IPP, which, however, have some trouble in finding a use at an industrial level also on account of the problems linked to the use of DMTMM (high costs, low availability, instability over time, etc.) [US 2013/0123508 A1, EP 1992364 A1]. DMTMM has a cost that is over three hundred times the average cost of equivalent activating agents currently used for the synthesis of polymers, biomaterials, and leather. Furthermore, quaternary ammonium salts of 2-halo-4,6-dialkoxy-1,3,5-triazines are generally unstable at room temperature over long periods [US 2003/0153785 A1] and may be subject to partial or total decomposition if they are not shipped and stored in adequate conditions. To garantee conservation thereof, DMTMM must be shipped and stored at −20° C. The cost of DMTMM is directly linked to the cost and availability of CDMT from which it is synthesised.

The literature regarding synthesis of 2-halo-4,6-dialkoxy-1,3,5-triazines principally regards the preparation of CDMT. One of the fundamental aspects of the synthesis of CDMT, as likewise of 2-halo-4,6-dialkoxy-1,3,5-triazines in general, is the control of the course of the reaction in order to minimize or eliminate completely formation of secondary products.

Currently, the only protocol for the synthesis of 2-halo-4,6-dialkoxy-1,3,5-triazines is described in US 2002/0123628 and regards the synthesis on a scale of some grams carried out with normal laboratory equipment. The reaction is generally conducted starting from a cyanuric chloride in the presence of an alcohol, prevalently methanol, and a base, preferably NaHCO$_3$. During the reaction, water and CO$_2$ are formed. In the document No. US 2002/0123628, the authors pose as basic requisite for obtaining good selectivity and yields of 2-halo-4,6-dialkoxy-1,3,5-triazines that the amount of water present at the start and at the end of the reaction should always be less than 2.5 mol per mole of cyanuric halogenide (compound of formula I, hereinafter also referred to simply as "I", in the reaction sheme presented below). Consequently, since water is a by-product of the reaction, to obtain high yields of CDMT according to the protocol described above, it is necessary for all the solvents to be distilled and anhydrified prior to use and possibly for the reactions to be conducted in an inert atmosphere. Furthermore, large amount of alcohol are required, used both as reagent and as solvent for reducing the viscosity of the system (ratio alcohol/I=5-50 mol/mol). At the end of the reaction, the product must be recovered by extraction with water/organic solvents and then anhydrified, and the organic solvent evaporated. Presented in the scheme appearing below is the synthesis of 2-halo-4,6-dialkoxy-1,3,5-triazines, together with the secondary products that may form during the reaction.

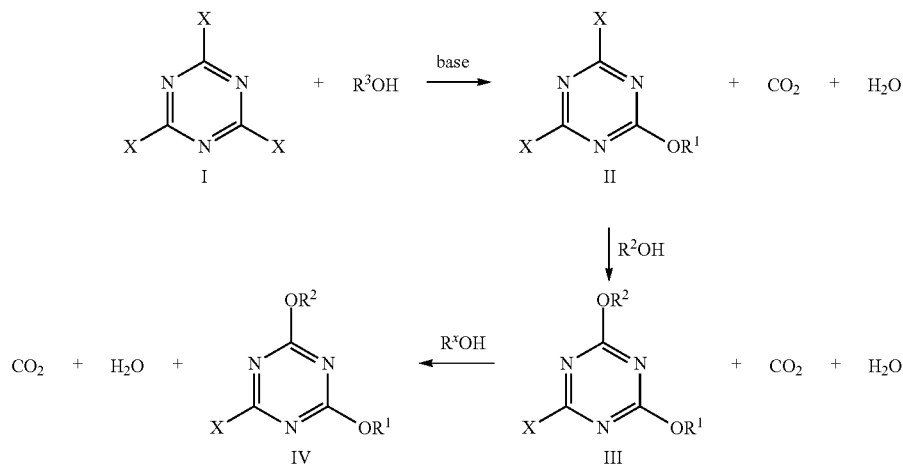

where:
R$^x$ is R$^2$ or R$^2$; R$^2$ and R$^2$ are chosen independently from:
—CH$_3$, —CH$_2$CH$_3$, —CH(CH$_3$)$_2$, —(CH$_2$)$_2$CH$_3$, —(CH$_2$)$_3$CH$_3$; and
X is Br$^-$ or Cl$^-$.

According to Dudley [J. Am. Chem. Soc., 1951, 73, 2986-2990] the addition of variable amounts of water for the synthesis of CDMT improves the homogeneity of the system (ratio I/base/H$_2$O/MeOH=1/2/2/8). However, the author does not analyse the evolution of the kinetics of formation of the compound of formula IV as the rate of addition of the reagents varies. On the basis of our studies it has been found that, if the addition of the compound of formula I is too fast (exothermic) variable percentages of the compound of formula IV are formed (from 5 to 25%), with consequent higher consumption of methanol. Consequently, this procedure calls for large amounts of methanol, with yields of less than 74%. J. Cronin [Synth. Commun., 1996, 26, 3491-3494] in his work presents a methodology employed exclusively for the synthesis of CDMT, which, according to the author, can be used for up to a maximum of 20 kg. However, no detail as regards scale up is presented, and in effect, we have been unable to reproduce Cronin's protocol for amounts exceeding 50 g of CDMT, and complex mixtures containing compounds of formulas II, III, and IV were produced in variable percentages.

SUMMARY OF THE INVENTION

A first purpose of the invention is to provide a method for the production of reagents to be used in the process of stabilization of collagen matrices and of condensation of natural and synthetic polymers, such as polyacrylic acid, polyethylene, cellulose, and/or modified celluloses, polysaccharides, starch, and lignin, by means of reactions of condensation, crosslinking, grafting, and curing.

In particular, the invention provides a method for the production of the active principle of one of the reagents that intervenes in the process of stabilization of collagen matrices, which may be derived from waste of foodstuff industry, and condensation of polymers, which also forms the subject of the invention. This active principle according to the invention is a 2-halo-4,6-dialkoxy-1,3,5-triazine, which in the presence of aliphatic, linear, branched, aromatic, cyclic, or heterocyclic tertiary amines activates reactions of condensation, crosslinking, grafting, and curing.

Forming the subject of the invention is also the method for the synthesis of 2-halo-4,6-dialkoxy-1,3,5-triazines that can be implemented on an industrial scale.

Moreover forming the subject of the invention is the use of said 2-halo-4,6-dialkoxy-1,3,5-triazines and of the compositions that include them as agents for activating reactions of condensation, crosslinking, grafting, and curing.

Also falling within the scope of the present invention is the use of 2-halo-4,6-dialkoxy-1,3,5-triazines in processes for tanning hides, where their application is particularly advantageous. In this particular form of reaction, the invention envisages that stabilization of the hide is obtained by means of reaction with two reagents, in succession or previously mixed, one of which comprises one or more 2-halo-4,6-dialkoxy-1,3,5-triazines, and the other comprises one or more linear, branched, aromatic, cyclic, heterocyclic alkyl tertiary amines.

Also forming the subject of the invention is leather obtained using this method, characterized in that it does not contain toxic residue produced by decomposition of the tanning agents used englobed in the matrix.

BRIEF DESCRIPTION OF THE SEVERAL VIEWS OF THE DRAWING

The FIGURE illustrates that on the basis of the protocol described herein, there has been monitored over time by means of GLC formation of the aspecific products of reaction, respectively the compounds of formulas II, III, and IV of the Dudley method according the prior art, for the various 2-halo-4,6-dialkoxy-1,3,5-triazines synthesized and the data for the synthesis of CDMT plotted in the graph.

DETAILED DESCRIPTION OF THE INVENTION

It has been found that compounds of formula III,

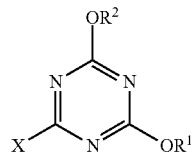

(III)

where:
$R^1$ and $R^2$ are independently chosen from: —$CH_3$, —$CH_2CH_3$, —$CH(CH_3)_2$, —$(CH_2)_2CH_3$, —$(CH_2)_3CH_3$; and
X is $Cl^-$ or $Br^-$ namely, 2-halo-4,6-dialkoxy-1,3,5-triazines, are able to act as agents for activating reactions of condensation, crosslinking, grafting, and curing and in processes of stabilization of collagen matrices, as well as of condensation of natural and synthetic polymers, such as cellulose, and/or modified celluloses, polysaccharides, starch, lignin, etc., and their application is very advantageous in terms of ease of use, economic convenience, and stability over time of these compounds.

Thus, through a specific method that uses them, which forms the subject of the invention described herein, it is possible to reduce the overall costs considerably as compared to the methods used for the same purpose in the prior art and reduce the environmental impact of the process, limiting the amount of solvents, energy, and time necessary for their preparation and implementation.

The method of stabilization of collagen matrices and of condensation of natural and synthetic polymers that forms the subject of the present invention hence presents as a methodology alternative to preparation using IPP.

In particular, the method of stabilization of collagen matrices and of condensation of polymers that forms the subject of the present invention is obtained from the reaction of two reagents, denoted, for the purposes of the present invention, as "first reagent", or "Reagent 1", and "second reagent", or "Reagent 2".

According to the present invention, Reagent 1 is a composition comprising:
a) at least one compound of formula III (2-halo-4,6-dialkoxy-1,3,5-triazine);
b) a buffer;
c) a salt;
d) a solvent.

According to the present invention, Reagent 2 is a composition comprising:
a) a tertiary amine;
b) a buffer;
c) a solvent.

Reagent 2 may further comprise an additive for the buffer.

Hence, forming the subject of the present invention are also the compositions of the aforesaid two reagents, Reagent 1 and Reagent 2, which are essential for implementation of the method according to the invention.

Reagent 1 is a composition comprising as active principle one or more 2-halo-4,6-dialkoxy-1,3,5-triazines in a concentration ranging between 0.1M and 1.0M. The composition that constitutes Reagent 1 also comprises a buffer, preferably a Good buffer, chosen in the group: MES, ACES, BES, BIS-Tris, MOPS, TEA, TAPSO, POPSO, TAPS, formiate, phosphate, succinate. The composition that constitutes Reagent 1 comprises a base or a salt of formula $X^+Y^-$, where $X^+$ is $Na^+$, $K^+$, or $Ag^+$, and $Y^-$ is: $ClO_4^-$, $BF_4^-$, $PF_6^-$, $CO_3^{2-}$, $Cl^-$, $HCO_3^-$.

The composition that constitutes Reagent 1 comprises a solvent chosen in the group of: aliphatic ethers, halogenates, alcohols, ketones, esters, aromatic or aliphatic hydrocarbons, amides, carbonates, DMSO, and water.

Reagent 2 is a composition comprising as active principle one or more linear, branched, cyclic, aromatic, heterocyclic tertiary amines, and/or their quaternary salts, in a concentration ranging between 0.1M and 1.0M. The composition that constitutes Reagent 2 also comprises a buffer, preferably a Good buffer, chosen in the group: HEPES, MOPS, TRIS, tri-Na-citrate, Tris-Cl, TAPS.

The composition that constitutes Reagent 2 comprises a solvent chosen in the group of: aliphatic ether, halogenate, alcohol, ketone, ester, aromatic or aliphatic hydrocarbon, amide, carbonate, DMSO, and water.

In some particularly preferred embodiments, Reagent 2 may further comprise additives for the buffer, which are chosen in the group: NaCl, $Na_2HPO_4$, NaOAc, KCl, SDS, glycine, boric acid, EDTA, and $NaN_3$.

The process of stabilization of the collagen matrices according to the invention finds application in multiple contexts of considerable technological and industrial interest.

Up to the present day, there does not exist any protocol that uses 2-halo-4,6-dialkoxytriazines in the presence of amines for stabilization of collagen. The present applicant has conducted tests that demonstrate that the method forming the subject of the invention enables crosslinking of powdered collagen dispersed in water by adding one after the other the two reagents, Reagent 1 and Reagent 2, as described in the examples provided hereinafter. From the results of the experimentation, it emerges clearly that the procedure adopted for crosslinking the collagen according to the invention conducted in the presence of Reagents 1 and 2, is notably superior to the one obtained with IPP. In particular, Reagents 1 and 2 have proved to present a better performance than aldehydes, glycerol, synthetic/natural crosslinking agents, carbodiimides, EDC/NHS, and quaternary ammonium salts of 2-halo-4,6-dialkoxy-1,3,5-triazines, which are currently used for stabilization of collagens according to the prior art, where normally the gelatinization temperature (Tg) does not exceed 80° C.

The above result is particularly important for the production of collagen tissues and materials with high thermal stability and their conservation in time for medical use and use in biotechnology (collagen, leather, tissues, corneas, etc.). On the basis of the results obtained for the reaction of crosslinking of collagen between phenethylamine and benzoic acid it may be pointed out that:

i) the IPP procedure presents limits of application in so far as not all the quaternary ammonium salts of 2-halo-4,6-dialkoxy-1,3,5-triazines can be synthesised, isolated, and used as activating agents;

ii) Reagents 1 and 2 enable the above difficulties to be overcome in the majority of the cases with the use of the procedure disclosed;

iii) in all comparable cases, 1,3,5-triazines provide conversions, performance, and characteristics that are equal or superior to those obtained with the corresponding IPP;

iv) the protocol of use of Reagents 1 and 2 may be formulated in the presence of various amines, and hence, according to the application, it is possible to choose the one available at the most advantageous market price;

v) Reagents 1 and 2 that do not present problems of activity linked to the nature of the solvent may moreover be used also in aqueous solvent;

vi) the protocol presented herein may be scaled up without substantial modifications from grams to kilograms and beyond; the effectiveness of the method according to the invention has moreover been verified for the reaction of condensation between benzoic acid and phenethylamine, presented in the scheme represented below as possible non-limiting example of condensation between a generic acid and a generic amine.

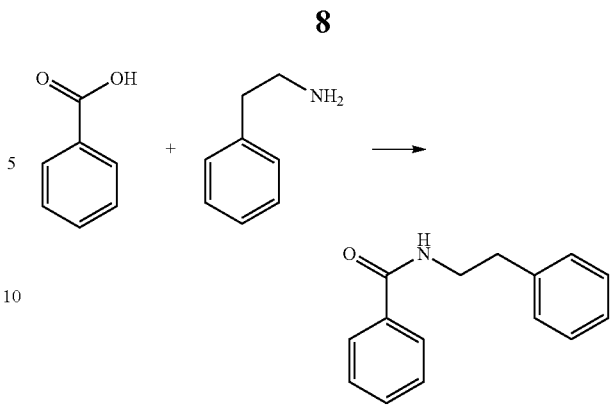

The effectiveness of the procedure according to the invention has moreover been verified in condensation reactions conducted on powdered bovine collagen, used as standard substrate for verifying the activity of the reagents of reactions of crosslinking, grafting, condensation, and curing, supplying data that are reproducible on collagen in other forms (liquid collagen, hydrolysed collagen, collagen fibres, solid matrix, etc.). It has been demonstrated that the use of additional crosslinking agents, such as formaldehyde, glutaraldehyde, glycerol, etc., is not necessary. The values of Tg obtained refer to stabilization of the collagen matrix obtained by exclusive crosslinking of the collagen with itself by the action of 2-halo-4,6-dialkoxy-1,3,5-triazines in the presence of amines and various additives.

It has moreover been found (Example 3) that the method, if conducted in the presence of chiral reagents, maintains enantioselectivity in the products. This characteristic is of fundamental importance for the synthesis of drugs, fragrances, active principles with high added value, etc.

In one embodiment, the present invention provides a method for stabilization of natural matrices, such as cellulose and/or modified celluloses. For instance, using Reagents 1 and 2, as specified in Example 5 of the experimental section, carboxymethylcellulose (CMC), which is commonly used for the production of biodegradable hydrogels [C. Demitri, International J. Polymer Science, 2013, 1-6] can be converted into a material that is not soluble in water, is biodegradable, and presents totally innovative characteristics. From a markedly hydrophilic matrix a highly hydrophobic material is obtained thanks to the high degree of crosslinking due to reaction of the acid and alcohol groups present in CMC, with formation of ester groups.

In another embodiment of the present invention, described in Example 6, the use of Reagents 1 and 2 is performed by grafting of natural polymers and synthetic polymers, to form polyamides, polyesters, and polythioesters (Example 6). In this embodiment, the procedure represents a valid alternative for the production of polyamides, polyesters, etc. In this way, the preparation of the polymers, instead of being conducted specifically for each polymer, enables synthesis of an aspecific base polymer, which, thanks to the subsequent derivatization or grafting, assumes specific characteristics. Consequently, in this way, starting from one and the same matrix and in a single step, it is possible to obtain a vast range of known and unknown polymeric products.

In a further, particularly preferred, embodiment, the method of stabilization of collagen according to the invention finds application in the sector of the tanning industry and of processing of animal skins, to enable their conservation and subsequent further processing. The method enables the pelts obtained according to the standard preliminary procedures to be treated in a single step with the two tanning reagents, namely, the first reagent, or Reagent 1, and the second reagent, or Reagent 2, described previously, where for both of the reagents the solvent is water, to obtain a collagen derivative with high thermal stability (Tg≥80° C.), as shown in Examples 10 et seq.

The two reagents in aqueous solution are essential for implementation of the tanning method according to the invention.

The method for tanning leather according to the present invention is suitable for obtaining leather from the skins of common slaughter animals, such as cattle, sheep, goats, and horses. The method is totally innovative and extremely simple to use, and moreover provides gelatinization temperatures (Tg) even higher than 100° C., which had never been obtained previously with alternative systems according to the prior art.

The method according to the invention envisages treatment of pelts, i.e., defleshed skin stripped of hair and ready for tanning, according to what is envisaged by the standard procedures used also for preparation of skin that is to be tanned with chromium (III) salts.

The pelt is then suspended in water.

Reagents 1 and 2, as defined previously, are added in the water bath containing the pelt in a concentration ranging between 3 and 22 wt % with respect to the weight of pelt set to react.

Reagents 1 and 2 can be added to the bath simultaneously, or in succession, in the order Reagent 1 and then Reagent 2. To obtain high Tg values, it is preferable for the addition of the two reagents to be carried out in two successive stages. Alternatively, the two reagents may be premixed in a homogenizer/reactor under stirring and with control of the temperature (10° C.<T<45° C.), and then used for tanning.

In the presence of Reagents 1 and 2, the pH of the tanning environment does not call for pre-acidification or neutralization since the treatment reaches its maximum effectiveness in a range of values of pH of between 5.5 and 8.5. Consequently, the specimens of pelt subjected to the tanning procedure according to the present invention do not need to undergo the prior pickling step, i.e., the preparatory step envisaged prior to chromium tanning, which is carried out by treating the pelts in a solution of salt and acid, more frequently formic acid and sulphuric acid, nor the subsequent basification.

At the end of the step of tanning conducted in the presence of 2-halo-4,6-dialkoxy-1,3,5-triazines and amines, the spent bath is emptied out of the drum or reactor used, and the latter is washed with 150-200 wt % of water, and the skins thus obtained are sent on to the subsequent processing steps.

Consequently, the process of tanning of the hide carried out with Reagents 1 and 2 of the present invention comprises the steps of:
  a) suspension of pelts in water in a reactor;
  b) addition of the two tanning reagents in water in a concentration ranging between 3 and 22 wt % with respect to the weight of the pelt set to react; and
  c) removal of the spent bath from the reactor and flushing of the reactor with water.

Furthermore, the leather obtained with the method according to the invention is suitable for undergoing the subsequent processes, such as neutralization, re-tanning, greasing, dyeing, etc.

The procedure described herein is totally metal-free, i.e., it is obtained without the use of any metal such as for example chromium, aluminium, iron, zirconium, titanium salts, etc., and does not undergo any contamination from formaldehyde or phenol, because it does not use these reagents or their derivatives in any way. Furthermore, by using 2-halo-4,6-dialkoxy-1,3,5-triazines, no acid treatment of the skins prior to the tanning process is required, thus also enabling omission of the subsequent basification step. In this way, the tanning process is obtained in a single step.

The tanning agents used in the method according to the invention, deriving from 2-halo-4,6-dialkoxy-1,3,5-triazines in the presence of amines, and buffer, as per the formulation of Reagents 1 and 2, are not equivalent to synthetic tannins since they are not withheld within the matrix, but act exclusively as crosslinking activators, in this way tanning the leather. The use of triazine derivatives according to the invention enables high Tg values to be to obtained in 1-4 h. However, the treatment can, for any type of particular need, be protracted also for longer times, without altering in any way the quality of the finished product. This technical feature represents an advantage over the classic processes of chromium tanning, the total duration of which varies, according to the type of leather treated, up to a maximum of 20-24 h.

The method according to the present invention, which uses as Reagent 2 a formulation containing a mixture of two or more amines, makes it possible to obtain a crosslinking agent having controlled action, which can be modulated in order to obtain leather with different characteristics.

The effectiveness of the method that uses Reagents 1 and 2 forming the subject of the invention has been demonstrated by means of specific crosslinking or tanning tests, conducted with the reagents on specimens of powdered bovine collagen. Experimentation with this substrate provides reproducible data on the effectiveness of the two reagents and of the corresponding method on solid collagen, i.e., on skins. In all cases, the Tg values obtained with the pelt specimens are similar to those obtained with powdered collagen and in any case comprised between 71° C. and 105° C. The effectiveness of Reagents 1 and 2, formulated according to what has been described above, has been verified also on specimens of bovine skins previously softened, stripped of hair, delimed, macerated, and defleshed (pelt) according to standard procedures used for the preparation of leather tanned with chromium (III) salts.

The methodology disclosed according to the present invention is free from problems due to the presence of substances harmful for health in the finished product since it is known that 2-halo-4,6-dialkoxy-1,3,5-triazines do not remain englobed in the matrix and/or reagents used and are eliminated during the washing cycles at the end of the reaction. Consequently, forming the subject of the invention is also the leather that can be obtained with the method of the invention, characterized in that it is without contaminants and harmful substances produced and accumulated in the matrix during the tanning process.

The effectiveness of the method according to the invention is widely demonstrated in the examples presented in the experimental section of the present description (Examples 13-23). The experimental data have shown that, using different embodiments of Reagent 1 and Reagent 2 according to the invention, Tg values of up to 105° C. were obtained, with excellent dyeability due to the perfectly white colour that characterizes all the specimens of skins treated with these 2-halo-4,6-dialkoxy-1,3,5-triazine derivatives.

From the present description it hence appears evident that falling within the scope of the invention is also the use of 2-halo-4,6-dialkoxy-1,3,5-triazines and of the compositions that comprise them as activating agents for reactions of crosslinking, grafting, curing, and condensation, in particular in the processes of collagen stabilization and of condensation of natural and synthetic polymers, such as for example polyacrylic acid, polyethylene, cellulose, and/or modified celluloses, polysaccharides, starch, and lignin.

Forming an integral part of the present invention is also the method of production of 2-halo-4,6-dialkoxy-1,3,5-triazines that act as activating agents in the reactions of crosslinking, grafting, curing, and condensation of the processes of stabilization of natural matrices such as cellulose, and/or modified celluloses, and collagen matrices according to the invention described previously.

Forming a further subject of the invention is the method for the production of 2-halo-4,6-dialkoxy-1,3,5-triazines, implemented on an industrial scale, in amounts of the order of kilograms or tonnes and optimization for the recovery or work up of the two products. Up to the present day, no batch or semi-batch process for the production of these compounds has been described.

Scale-up of the process of production is a fundamental practice for evaluating and solving the problems linked to passage from the production of a few grams (laboratory scale), to the production of kilograms or tonnes (industrial scale).

It has been shown that in the process of production of 2-halo-4,6-dialkoxy-1,3,5-triazines, by controlling the rate of addition of the reagents and the temperature of reaction it is possible to optimize the method considerably. This makes it possible to avoid the use of anhydros solvents, the need to operate in an inert atmosphere, etc. Furthermore, by controlling these parameters, a product with a high degree of purity is obtained, simply by washing with water, without the use of organic solvents, and/or other techniques of purification such as ricristallization. Consequently, this process for synthesis on an industrial scale of 2-halo-4,6-dialkoxy-1,3,5-triazines is obtained with considerably reduced costs as compared to current known processes, optimizing the operating parameters of the process of synthesis and recovery of the product in kilograms per day or tonnes per day.

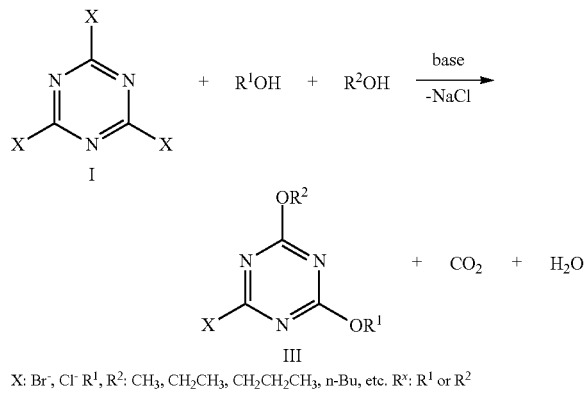

X: Br⁻, Cl⁻ R¹, R²: CH₃, CH₂CH₃, CH₂CH₂CH₃, n-Bu, etc. Rˣ: R¹ or R²

The method for the synthesis of 2-halo-4,6-dialkoxy-1,3,5 triazines of formula III according to the invention, comprises the steps of:
  reaction of substitution between cyanhydric halogenide of formula I and linear or branched aliphatic alcohol, in single phase, in the presence of a base;
  quenching of the reaction by means of addition of water and stirring;
  filtration;
  drying.

The method hence envisages a reaction of substitution between a cyanuric halogenide (Cl⁻, F⁻, Br⁻) of formula I and a linear or branched aliphatic alcohol in the presence of a base at a temperature ranging between 45° C. and 130° C. for a duration of 5-48 h according to the alcohol used.

The amount of water added is important since it affects: i) homogeneity of the reaction mixture; ii) control of heating. According to our results, the synthesis of 2-halo-4,6-dialkoxy-1,3,5-triazines is preferably carried out in the presence of 0-7 mol of water per mole of the compound of formula I, water which in effect favours the homogeneity of the reaction mixture providing high selectivity and purity in the compound of formula III. The presence of water enables reduction of the amount of alcohol used such that, for 1 mole of the compound of formula I moderate amounts of alcohol of between 1-5 Eq are sufficient.

The reaction may be conducted in the presence of any linear or branched aliphatic alcohol; for example, $R^1$, $R^2$: $CH_3$, $CH_2CH_3$, $CH(CH_3)_2$, $(CH_2)_2CH_3$, $(CH_2)_3CH_3$, where $R^1$ may be equal to or different from $R^2$, of any degree of purity commercially available without further purification (amounts of water variable in the range 0.03-0.5%) and without affecting in any way the selectivity or yield in the desired triazine. The base may be any carbonate; $NaHCO_3$ is preferably used. Normally, for the synthesis of 2-halo-4,6-dialkoxy-1,3,5-triazines the ratio between the reagents (compound of formula I, base, water, and solvent) is fixed in a very precise way. According to the invention it is possible to use ratios between the reagents I/base/water/solvent of between 1/1/0/4 and 1/5/7/12 obtaining, in all cases, compounds of formula III with yields and purities higher than 90%, guaranteeing a further versatility and reduction of the error margins for its application at an industrial level.

It is of fundamental importance for the addition of the reagents to be carried out at a certain rate, with a good control of the temperature and of stirring so as to prevent formation of non-desired products and intermediates, i.e., the compounds of formulas II and IV that are normally formed with the method according to the prior art [Dudley, 1951]. This has been obtained using auger dispensers and indicators for control of the temperature. When the addition of the compound of formula I is through, the reaction temperature gradually goes back to room temperature. This must be avoided, in so far as insufficient heating after the addition arrests the reaction with formation of high percentages of aspecific products.

Normally, the reaction is conducted at temperatures of between 45 and 130° C., according to the alcohol used. On the basis of the protocol described herein, there has been monitored over time by means of GLC formation of the aspecific products of reaction, respectively the compounds of formulas II, III, and IV of the Dudley method according the prior art, for the various 2-halo-4,6-dialkoxy-1,3,5,-triazines synthesized and, by way of example, the data for the synthesis of CDMT are plotted in the graph of the FIGURE. The reagents are added in the reactor where the reaction occurs in a specific order: first 1-5 Eq of base are introduced into the reactor together with 1-5 Eq of ROH (methanol, ethanol, isopropanol, butanol, etc.) and 0-7 Eq of water. Under vigorous stirring, 1 Eq of the compound of formula I is added in 0.5-3 h and, once addition of the compound of formula I is through, the mixture is heated at 45-130° C. under stirring for 5-48 h. The amount of water reduces the viscosity of the reaction mixture; however, the system is heterogeneoous, so that it is necessary to have available an adequate stirring system able to mix a suspension having a viscosity ranging from low to medium. After 5-48 h the reaction mixture is stopped by adding 1-5 volumes of water and subsequently stirred for 0-480 min. The suspension is transferred into a filtering device, or Nutsche filter, separated from the solution, and dried. The method according to the invention enables recovery of 2-halo-4,6-dialkoxy-1,3,5-triazines with a yield higher than 90% and a purity of 92-97% (3-8% of water). After the reaction, the reactor is cleaned and is ready for another lot of reagents.

In a particularly preferred embodiment of the invention aimed at obtaining amounts of product of and order exceeding kilograms, the reaction is conducted in a batch reactor with ellipsoidal bottom, of adequate capacity, equipped with a system for addition of the reagents. The reaction between the compound of formula I and an alcohol, in the presence of a base, is initially an exothermic reaction with development of $CO_2$. The heat developed enables the reaction to proceed for the duration of the additions. The temperature must be effectively controlled in such a way that within the reactor the relation 10 C<T<45° C. is satisfied. This is performed via control of the temperature using reactors with an external/internal cooling system. To determine the dimensions of the reactor, also the amount of water used for stopping the reaction and purifying the products must be taken into account. For this reason, the total internal volume must be at least 1.5-2.0 times the total volume of the reagents. For instance, for a production of 10 kg, the volume of the reactor must be comprised between 0.2 and 1 m$^3$.

The reactors selected are normal pressurized containers, reinforced, and lined with steel. Particular linings with high resistance to corrosion may be used when necessary. The reactors used have an external and/or internal coil system with appropriate heat-exchange properties for heating or cooling the reaction and condensing the solvent vapours, with possible recycling of the condensed vapours. The reactors must moreover have a blade stirrer, inlets, and outlets that connect it to other equipment, sensors for detecting temperature, pressure, pH, and viscosity, bypass loops to monitor the reaction over time (GLC).

The products are recovered by filtration, washing, and drying. Typically, the products are present in the reaction mixture as suspended solids. After cooling and purification or work-up, the reaction mixture is transferred into a filtering device or Nutsche filter for drying and recovery of the product. The volume of the filter may be configured for receiving an entire load from the reactor. The main flow of the reaction, containing the solvent, may be collected separataly from the purification solvent (water) and recycled in the batch reactor (further fresh alcohol is added to obtain the required stoichiometry).

The availablility of a reagent having low or zero toxicity, which is able to crosslink the collagen supplying highly stable matrices, i.e., highly stable to temperature (Tg) and hence highly resistance to degradation over time, constitutes an important result for a wide range of applications in pharmaceutical, biomedical field, etc.

Experimental Part

The invention will be described in what follows by way of non-limiting illustration, with particular reference to some examples.

In the examples presented hereinafter for non-limiting illustrative purposes, Reagents 1 and 2 according to the invention are identified and represented with the codes AaBbCcDdEe and FfGgHhEe, where a, b, c, d, . . . =0, 1, 2, 3, 4, . . . n.

In particular, for Reagent 1:
A identifies 2,4-dialkoxy-1,3,5-triazines; for example, $A_1$: 2-chloro-4,6-dimethoxy-1,3,5-triazine; $A_2$: 2-chloro-4,6-diethoxy-1,3,5-triazine; $A_3$: 2-chloro-4methyl-6-ethyl-1,3,5-triazine, etc.
B identifies the buffer, preferably a Good buffer; for example, $B_1$: MES; $B_2$: ACES; $B_3$: BES, $B_4$: POPSO; $B_5$: TRIS; $B_6$: HEPPSO; $B_7$: TAPS; $B_8$: Tris-NaCitrate.
C identifies the cation of an inorganic salt $X^+$; for example, $C_1$: $Na^+$; $C_2$: $K^+$; $C_3$: $Ag^+$.
D identifies the anion of an inorganic salt $Y^-$; for example, $D_1$: $ClO_4^-$; $D_2$: $BF_4^-$; $D_3$: $Cl^-$; etc.
E identifies the solvent; for example, $E_1$: aliphatic ether; $E_2$: alcohol; $E_3$: water; $E_4$: acetone; $E_5$: THF; etc.

For Reagent 2:
F identifies the aliphatic, linear, branched, cyclic, aromatic, heterocyclic, amine and/or its quaternary salts, for example, $F_1$: TMA (trimethylamine); $F_2$: TEA (triethylamine), $F_3$: DEMA (diethylmethylamine); $F_4$: NMM (N-methylmorpholine); $F_5$: NEM (N-ethylmorpholine); $F_6$: MPD (methylpyrrolidine); $F_7$: MP (methylpiperidine); etc.
G identifies the buffer, preferably a Good buffer; for example, $G_1$: BES; $G_2$: MOPS; $G_3$: TRIS; $G_4$: POPSO, $G_5$: TAPS; $G_6$: Tris-NaCitrate; etc.
H identifies the additives for the buffer; for example, $H_1$: NaCl; $H_2$: $Na_2HPO_4$; $H_3$: NaOAc; $H_4$: KCl; $H_5$: SDS; etc.
E identifies the solvent; for example, $E_1$: aliphatic ether; $E_2$: alcohol; $E_3$: water; $E_4$: acetone; $E_5$: THF; etc.

All the analyses presented herein were carried out with a gas chromatograph Agilent Technologies 6850, using a flame-ionization detector, equipped with an HP5 capillary column (5% methylphenylsilicone; conditions of analysis: 50° C. for 4 min, then 20° C./min up to 250° C.). The 1H and $^{13}$C NMR spectra were recorded with a spectrometer Bruker Avance 300 operating at 300.11 MHz for the proton spectrum and at 75.03 MHz for the carbon spectrum. The FT-IR spectra (KBr tablet) were obtained with a spectrophotometer Perkin Elmer "Spectrum One". The DSC analyses were determined with DSC Netzsch STA 409 PC, melting point Buchi 535. The enantiomeric excesses were measured by means of chiral HPLC using a CHIRALCEL OD-H (250 mm×4.6 mm) with an Agilent 1100 HPLC equipped with a 254-nm UV detector.

Example 1

Condensation Between Benzoic Acid and Phenethylamine (Test 2 of Table 1) by Means of a Procedure that uses Reagent 1 ($A_1B_1C_2D_3E_3$) and Reagent 2 ($F_6G_2H_2E_3$)

In a flask provided with magnetic stirring there were dissolved 293.1 mg (2.4 mmol) of benzoic acid in 15 mL of methanol. To the solution there were added 300 μL (2.4 mmol) 2 of phenethylamine and 2.4 mL of Reagent 1. Finally, there were added 2.4 mL of Reagent 2. After 2 h a sample was taken for monitoring conversion, which was found to be 60%; then, the solvent was evaporated using a rotary evaporator. The solid residue was dissolved in diethyl ether (30 mL), and subsequently washed with a saturated solution of $Na_2CO_3$, water, a 1N solution of HCl, and a saturated solution of NaCl, anhydrified with $MgSO_4$, and filtered. The solution was dried off to obtain the product in the form of a white solid (450.6 mg, 2 mmol, yield 83%).

$^1$H NMR (CDCl$_3$, 300 MHz, ppm) $\delta_H$=: 7.72-7.31 (m, 2H), 7.52-7.23 (m, 8H), 6.26 (br s, 1H), 3.73 (m, 2H), 2.95 (t, 2H); $^{13}$C NMR (75 MHz, CDCl$_3$, ppm) $\delta_c$:. 167.43, 138.86, 134.60, 131.33, 128.75, 128.65, 128.43, 126.76, 126.52, 41.10, 35.67.

Formulation of Reagent 1 (A$_1$B$_1$C$_2$D$_3$E$_3$): 1.0M solution of 2-chloro-4,6-dimethoxy-1,3,5-triazine, and of 10 wt % of MES, 0.5 wt % of KCl, and water.

Formulation of Reagent 2 (F$_6$G$_2$H$_2$E$_3$): 1.0M solution of MPD, 0.5-0.8 wt % of MOPS, 0.5-1.5 wt % of Na$_2$HPO$_4$, and water.

Example 1

Comparative Test. Reaction of Condensation between Benzoic Acid and Phenethylamine (Test 1 of Table 1) with DMT-MPD with IPP Method Synthesis of DMT-MPD In a flask provided with magnetic stirring there were introduced 500 mg (2.85 mmol) of CDMT dissloved in 10 mL of THF to which there were added drop by drop 300 μL (2.85 mmol) of MPD. After 10 min a white precipitate was obtained, which was recovered by filtration. The NMR analyses, in various solvents, highlighted that the product was not stable in solution, and hence it was not possible to carry out coupling with this reagent.

TABLE 1

Coupling reaction of benzoic acid and phenethylamine in the presence of triazine quaternary ammonium salts obtained with IPP and with the method that uses Reagent 1 and Reagent 2

| Test | Activator | t (h) | Conv. (%)[a] |
|---|---|---|---|
| 1 | DMT-MPD[b] | — | — |
| 2 | A$_1$B$_1$C$_2$D$_3$E$_3$/F$_6$G$_2$H$_2$E$_3$ | 1 h | 60 |
| 3 | DET-EM[b] | — | — |
| 4 | A$_2$B$_2$C$_2$D$_1$E$_1$/F$_5$G$_4$H$_1$E$_1$ | 24 h | 60 |
| 5 | DET-TMA[b] | — | — |
| 6 | A$_2$B$_2$C$_2$D$_1$E$_3$/F$_1$G$_4$H$_1$E$_3$ | 1 h | 100 |
| 7 | DMT-MP | 2 h | 81 |
| 8 | A$_1$B$_3$C$_2$D$_1$E$_4$/F$_7$G$_4$H$_1$E$_4$ | 2 h | 90 |
| 9 | DET-TMA | 2 h | 98 |
| 10 | A$_1$B$_1$C$_2$D$_2$E$_5$/F$_1$G$_4$H$_1$E$_5$ | 2 h | 100 |
| 11 | DET-MM[b] | — | — |
| 12 | A$_2$B$_2$C$_2$D$_1$E$_3$/F$_4$G$_3$H$_1$E$_3$ | 2 h | 70 |
| 13 | DMT-MM[c] | 2 h | 96 |
| 14 | A$_1$B$_4$C$_2$D$_2$E$_5$/F$_4$G$_3$H$_1$E$_5$ | 2 h | 100 |
| 15 | DET-EM | 24 h | 76 |
| 16 | A$_1$B$_0$C$_2$D$_2$E$_4$/F$_5$G$_4$H$_1$E$_4$ | 24 h | 82 |

Conditions of reaction: benzoic acid (1 Eq), phenethylamine (1 Eq), condensing agent (1 Eq).
[a]Conversion calculated by means of GLC with 156 mg (1 mmol) of n-undecane as internal standard.
[b]It was not possible to isolate the quaternary ammonium salt according to IPP.
[c]Commercially available.

Example 2

Comparative Test. Condensation Between Benzoic Acid and Phenethylamine (Test 7 of Table 1) by Means of IPP In a flask provided with magnetic stirring there were dissolved 293.1 mg (2.4 mmol) of benzoic acid in 15 mL of methanol. To the solution there were added 300 μL (2.4 mmol) of phenethylamine and 692 mg (2.4 mmol) of DMT-MP obtained with IPP. After 2 h a sample was taken for monitoring conversion, which was found to be 81%; then, the solvent was evaporated using a rotary evaporator. The solid residue was dissolved in diethyl ether (30 mL), and subsequently washed with a saturated solution of Na$_2$CO$_3$, water, a 1N solution of HCl, and a saturated solution of NaCl and then anhydrified in MgSO$_4$, and filtered. The solution was dried off to obtain the product as white solid (405.5 mg, 1.8 mmol, yield 75%).

$^1$H NMR (CDCl$_3$, 300 MHz, ppm) $\delta_H$: 7.72-7.31 (m, $^2$H), 7.52-7.23 (m, 8H), 6.26 (br s, 1H), 3.73 (m, 2H), 2.95 (t, 2H); $^{13}$C NMR (75 MHz, CDCl$_3$, ppm) $\delta_c$: 167.43, 138.86, 134.60, 131.33, 128.75, 128.65, 128.43, 126.76, 126.52, 41.10, 35.67.

Example 3

Production of Chiral Amides with the Method that uses Reagent 1 (A$_2$B$_3$C$_1$D$_1$E$_3$) and Reagent 2 (F$_4$G$_3$H$_1$E$_3$)

In a flask provided with magnetic stirring there were dissolved 200 mg (0.51 mmol) of 2-methyl-3-p-anisyl propanoic acid in 15 mL of methanol. To the solution there were added 55 μL (0.6 mmol) of aniline, 0.5 mL of Reagent 1 and, finally, 0.5 mL of Reagent 2. After 24 h the solvent was evaporated using a rotary evaporator.

The solid residue was dissolved in ethyl ether (30 mL), and subsequently washed with a saturated solution of Na$_2$CO$_3$, water, a 1N solution of HCl, and a saturated solution of NaCl, and then anhydrified with MgSO$_4$, and filtered. The solution was then dried off to obtain the product in the form of a yellow liquid with a yield of 75% (101 mg, 0.375 mmol).

$^1$H NMR (CDCl$_3$, 300 MHz, ppm) $\delta_H$: 7.33-7.26 (m, $^2$H), 7.24-7.14 (m, 2H), 7.07-7.01 (m, 2H),7.01-6.95 (m, 1H), 6.75 (d, 2H), 3.69 (s, 3H), 2.95-2.80 (m, 1H), 2.70-2.56 (m, 1H), 2.55-2.35 (m, 1H), 1.19 (d, 3H); $^{13}$C NMR (CDCl$_3$, 75 MHz, ppm) $\delta_c$: 172.95, 157.17, 136.68, 130.66, 128.89, 127.85, 123.18, 118.96, 112.91, 54.23, 44.02, 38.71, 16.67; HPLC: and.and. 96%, CHIRACEL OD-H column, n-hexane/isopropanol 92/8, 0.8 mL/min, $t_R$=17.15 min (lower) and $t_R$=21.2 min (upper).

Formulation of Reagent 1 (A$_2$B$_3$C$_1$D$_1$E$_3$): 1.0M solution of 2-chloro-4,6-diethoxy-1,3,5-triazine, and of 0-6 wt % of BES, 0.5 wt % of NaClO$_4$, and water.

Formulation of Reagent 2 (F$_4$G$_3$H$_1$E$_3$): 0.5M solution of NMM, 0.1-0.8 wt % of Tris, 0.5-2.5 wt % of NaCl, and water.

Example 4

Funtionalization with Aniline of Polyacrylic Acid with the Method that Uses Reagent 1 (A$_1$B$_4$C$_2$D$_1$E$_3$) and Reagent 2 (F$_4$G$_6$H$_2$E$_3$)

In a flask provided with magnetic stirring there were dissolved 60 mg (1.3×10$^{-4}$ mmol) of PAA (MW=450000) and 190 μL (2.1 mmol) of aniline in 35 mL of methanol.

To the solution there were then added 2.1 mL of Reagent 1 and 2.1 mL of Reagent 2. The solution was left under stirring for 24 h and then the solid was filtered, washed, dried, and analysed by means of $^1$H NMR. Formulation of Reagent 1 (A$_1$B$_4$C$_2$D$_1$E$_3$): 0.7M solution of 2-chloro-4,6,dimethoxy-1,3,5-triazine, and of 0-6 wt % of POPSO, 0.5-1.0 wt % of KClO$_4$, and water.

Formulation of Reagent 2 (F$_4$G$_6$H$_2$E$_3$): 0.7M solution of NMM, 0.1-5 wt % of Tris NaCitrate, 0.7-2.3 wt % of Na$_2$HPO$_4$, and water.

Example 5

Crosslinking of CMC with the Method that uses Reagent 1 ($A_1B_4C_2D_1E_3$) and Reagent 2 ($F_4G_6H_2E_3$)

In a flask provided with magnetic stirring there were dissolved 279 mg of CMC (carboxymethylcellulose with carboxylation degree of 0.7) in 25 mL of water. To the solution there were then added 3 mL of Reagent 1 and 3 mL of Reagent 2. The solution was left under stirring for 24 h, and then the aqueous phase was evaporated by means of a high-vacuum pump. The solid obtained was washed with water and characterized by means of FT-IR. FT-IR: 3200, 1750-1735, 1602, 1020 cm$^{-1}$ Formulation of Reagent 1 ($A_1B_4C_2D_1E_3$): 0.5M solution of 2-chloro-4,6,dimethoxy-1,3,5-triazine, and of 0-6 wt % of POPSO, 0.5-1.0 wt % of $KClO_4$, and water.

Formulation of Reagent 2 ($F_4G_6H_2E_3$): 0.5M solution of NMM, and of 0.1-5 wt % of Tris NaCitrate, 0.7-2.3 wt % of $Na_2HPO_4$, and water.

Example 6

Funtionalization with Methanol of Polyacrylic Acid with the Method that uses Reagent 1 ($A_2B_4C_2D_1E_3$) and Reagent 2 ($F_4G_6H_2E_3$)

In a flask provided with magnetic stirring there were dissolved 1.65 g ($3.8 \times 10^{-2}$ mmol) of an aqueous solution at 35% of sodium salt of polyacrylic acid (PAANa, MW=15000) and 2 mL of methanol in 60 mL of water. To the solution there were then added 5 mL of Reagent 1 and 5 mL of Reagent 2. The solution was left under stirring for 24 h, and washed with etyl ether.

The aqueous phase was concentrated using a high-vacuum pump, and the solid obtained was analysed by means of $^1$H NMR.

$^1$H NMR (D20, 300 MHz, ppm) $\delta_H$: 2.94 (s, 0.48H), 2.47 (br s, 1H), 1.66 (m, 2H).

Formulation of Reagent 1 ($A_2B_4C_2D_1E_3$): 0.2M solution of 2-chloro-4,6-diethoxy-1,3,5-triazine, and of 0-6 wt % of POPSO, 0.5-1.0 wt % of $KClO_4$, and water.

Formulation of Reagent 2 ($F_4G_6H_2E_3$): 0.2M solution of NMM, 0.1-5 wt % of Tris NaCitrate, 0.7-2.3 wt % of $Na_2HPO_4$, and water.

Example 7

General Procedure for the Synthesis of 2-halo-4,6-dialkoxy-1,3,5-triazines

In a reactor as described previously, there were introduced by means of an auger dispenser and/or a dispenser for liquids, 1-5 Eq of base, 4-12 Eq of ROH (methanol, ethanol, isopropanol, butanol, etc.), and 0-7 Eq of water. Under stirring 1 Eq of cyanuric halogenide was added through an auger dispenser (time of additions 0.5-3 h), and then the mixture was heated at 45-130° C. for 5-48 h. At the end of the reaction work-up was carried out by adding 1-5 volumes of water with subsequent stirring for 0-480 min. The suspension was filtered, and the product collected and dried in a vacuum. 2-halo-4,6-dialkoxy-1,3,5-triazines were recovered with a yield of 85-90% and a purity of 92-97% (3-8% of water). This method was used up to 150 kg of 2-halo-4,6-dialkoxy-1,3,5-triazines. For larger production volumes, it is recommended to arrange a number of reactors side by side in parallel.

Example 8

Synthesis of 2-chloro-4,6-dimethoxy-1,3,5-triazine (CDMT)

CDMT was synthesized using the general procedure described above (Example 7): in a reactor as described previously, there were introduced by means of an auger dispenser and/or a dispenser for liquids, 36 kg of $NaHCO_3$, 9.0 L of methanol, and 7.5 L of water. Then, there were introduced under stirring by means of an auger dispenser 10 kg of cyanuric chloride in approx. 2-3 h and then the mixture was heated at 100° C. for 36 h. At the end of the reaction, the work-up was carried out by adding 1-5 volumes of water (9-45 L) with subsequent stirring for 480 min. The suspension was filtered, and the product collected and dried in a vacuum. An amount of 8.5 kg (48.3 mol) was recovered with a yield of 89.5% and a purity of 96.7% (3.3% of water). This method was used up to 150 kg of CDMT. For larger production volumes, it is recommended to arrange a number of reactors side by side in parallel.

$^1$H NMR (CDCl$_3$, 300 MHz, ppm) $\delta_H$: 4.07; $^{13}$C NMR (75 MHz, CDCl$_3$, ppm) $\delta_c$: 172.72, 172.54, 56.04. FT-IR: 1540, 928, 806 cm$^{-1}$ m.p.: 75.2° C.

Example 9

Synthesis of 2-Chloro-4,6-Diethoxy-1,3,5-Triazine (CDET)

The CDET was synthesized using the general procedure described above (Example 7): in a reactor as described previously, there were introduced by means of an auger dispenser and/or dispenser for liquids, 32.4 kg of $KHCO_3$, 12.6 L of ethanol, and 9.7 L of water. Then, there were introduced under stirring by means of an auger dispenser 10 kg of cyanuric chloride in approximately 2-3 h, and then the mixture was heated at 120° C. for 48 h. At the end of the reaction work-up was carried out by adding 1-5 volumes of water (9-45 L) with subsequent stirring for 480 min. The suspension was filtered, and the product was collected and dried in a vacuum. An amount of 10.0 kg (49.4 mol) was recovered with a yield of 91.5% and a purity of 96.8% (3.2% of water). This method was used up to 150 kg of CDET. For larger production volumes, it is recommended to set a number of reactors side by side in parallel.

$^1$H NMR (CDCl$_3$, 300 MHz, ppm) $\delta_H$: 4.47 (q, 4H), 1.40 (t, 6H); $^{13}$C NMR (75 MHz, CDCl$_3$, ppm) $\delta_c$: 172.7, 172.1, 65.5, 14.2.

IR: 1554, 1325, 809 cm$^{-1}$ m.p.: 145° C.

TABLE 2

Crosslinking of powdered collagen with triazine quaternary ammonium salts obtained with IPP or with Reagent 1 and Reagent 2.

| Test | Activator | Tg (° C.)[a] |
|---|---|---|
| 1 | DMT-MPD[b] | — |
| 2 | $A_1B_1C_2D_3/F_6G_2H_2$ | 101 |
| 3 | DET-MM[b] | — |

TABLE 2-continued

Crosslinking of powdered collagen with triazine quaternary ammonium salts obtained with IPP or with Reagent 1 and Reagent 2.

| Test | Activator | Tg (° C.)[a] |
|---|---|---|
| 4 | $A_2B_3C_1D_1/F_4G_3H_1$ | 85 |
| 5 | DET-EM[b] | — |
| 6 | $A_2B_2C_2D_1/F_5G_4H_3$ | 103 |
| 7 | DET-TMA[b] | — |
| 8 | $A_2B_2C_2D_1/F_1F_6G_4H_1$ | 89 |
| 9 | DMT-MP | 87 |
| 10 | $A_1B_3C_2D_1/F_7G_6H_5$ | 89 |
| 11 | DTM-EM | 93 |
| 12 | $A_1B_5C_2D_1/F_5G_5H_1$ | 104 |
| 13 | DMT-EP | 92 |
| 14 | $A_1B_3C_2D_1/F_8G_2H_2$ | 95 |
| 15 | DMT-TEA[b] | — |
| 16 | $A_1B_3C_2D_1/F_2G_2H_3$ | 101 |
| 17 | DET-TMA | 89 |
| 18 | $A_2B_3C_2D_1/F_1G_5H_1$ | 87 |
| 19 | DMT-MM | 87 |
| 20 | $A_1B_4C_2D_1/F_4G_4H_2$ | 95 |

Conditions of reaction: powdered collagen;
solvent: water; time of reaction: 4 h; T(° C.): 25° C.
[a]Tg determined by means of DSC analysis.
[b]It was not possible to isolate the quaternary ammonium salt according to IPP.

Example 10

Tanning of powdered collagen with Reagent 1 ($A_1B_1C_2D_3$) and Reagent 2 ($F_6G_2H_2$), Test 2 of Table 2

In a 50-ml beaker there were added 500 mg of collagen, 25 mL of distilled water, and 0.6-12 mL of Reagent 1 and subsequently 0.6-12 mL of Reagent 2. The system was set under stirring at room temperature and the pH monitored every 60 min. After 4 h the suspension was filtered with a Buchner filter and washed with 50 ml of distilled water. The collagen treated was then analysed by means of DSC, to provide a Tg value of 85-101° C. as the concentration of reagents used varies.

Formulation of Reagent 1 ($A_1B_1C_2D_3$): 0.5M solution of 2-chloro-4,6-dimethoxy-1,3,5-triazine, and of 10 wt % of MES, 0.5 wt % of KCl, and water.

Formulation of Reagent 2 ($F_6G_2H_2$): 0.5M solution of MPD, 0.5-0.8% of MOPS, 0.5-1.5% of $Na_2HPO_4$, and water.

Example 11

Tanning of Leather with Reagent 1 ($A_1B_1C_2D_3$) and Reagent 2 ($F_6G_2H_2$)

A piece of skin of approximately 100 g softened, limed/delimed, macerated, and defleshed (pelt) according to the normal industrial procedures, was treated as described in what follows. A piece of pelt of approximately 100 g was put in a drum in the presence of 100 mL of water at room temperature. The system was set in rotation and subsequently there were added Reagent 1 and Reagent 2 (in concentrations ranging from 3.0% to 22%). After 4 h the bath was poured off, and the system washed twice with abundant water. Tg=83° C.-103° C. as the concentration of Reagents 1 and 2 used varies.

Example 12

Tanning of powdered collagen with Reagent 1 ($A_2B_3C_1D_1$) and Reagent 2 ($F_4G_3H_1$), Test 4, Table 2

The test was conducted in a way similar to what is described in Example 10.

Formulation of Reagent 1 ($A_2B_3C_1D_1$): 1.0M solution of 2-chloro-4,6-diethoxy-1,3,5-triazine, and of the 0-6 wt % of BES, 0.5 wt % of $NaClO_4$, and water Formulation of Reagent 2 ($F_4G_3H_1$): 0.5M solution of NMM, 0.1-0.8 wt % of Tris, 0.5-1.5 wt % of NaCl, and water.

Tg=73° C.-85° C. as the concentration of Reagents 1 and 2 used varies.

Example 13

Tanning of Leather with Reagent 1 ($A_2B_3C_1D_1$) and Reagent 2 ($F_4G_3H_1$)

The test was conducted in a way similar to what is described in Example 11, where Reagent 1 and Reagent 2 were formulated in a way similar to what is described in Example 12.

Tg=71° C.-87° C. as the concentration of Reagents 1 and 2 used varies.

Example 14

Tanning of Powdered Collagen with Reagent 1 ($A_2B_2C_2D_1$) and Reagent 2 ($F_5G_4H_3$), Test 6 of Table 2

The test was conducted in a way similar to what is described in Example 10.

Formulation of Reagent 1 ($A_2B_2C_2D_1$): 0.7M solution of 2-chloro-4,6-diethoxy-1,3,5-triazine, and of 0-6 wt % of ACES, 0.5-1.0 wt % of $KClO_4$, and water;

Formulation of Reagent 2 ($F_5G_4H_3$): 0.7M solution of NEM, 0.1-0.8 wt % of POPSO, 0.5-2.5 wt % of NaOAc, and water. Tg=93° C.-103° C. as the concentration of Reagents 1 and 2 used varies.

Example 15

Tanning of Leather with Reagent 1 ($A_2B_2C_2D_1$) and Reagent 2 ($F_5G_4H_3$)

The test was conducted in a way similar to what is described in Example 11, where Reagent 1 and Reagent 2 are formulated in a way similar to what is described in Example 14.

Tg=90° C.-105° C. as the concentration of Reagents 1 and 2 used varies.

Example 16

Tanning of Powdered Collagen with Reagent 1 ($A_2B_2C_2D_1$) and Reagent 2 ($F_6F_1G_4H_1$), Test 8 of Table 2

The test was conducted in a way similar to what is described in Example 10.

Formulation of Reagent 1 ($A_2B_2C_2D_1$): 0.8M solution of 2-chloro-4,6-diethoxy-1,3,5-triazine, and of 0-6 wt % of ACES, 0.5-1.0 wt % of $KClO_4$, and water.

Formulation of Reagent 2 ($F_6F_1G_4H_1$): 0.7M solution of MPD, 0.3 M of TMA, 0.1-0.8 wt % of POPSO, 0.5-2.5 wt % of NaCl, and water.

Tg=83° C.-89° C. as the concentration of Reagents 1 and 2 used varies.

Example 17

Tanning of Leather with Reagent 1 ($A_2B_2C_2D_1$) and Reagent 2 ($F_6F_1G_4H_1$)

The test was conducted in a way similar to what is described in Example 11, where Reagent 1 and Reagent 2 are formulated in a way similar to what is described in Example 16.

Tg=81° C.-90° C. as the concentration of Reagents 1 and 2 used varies.

Example 18

Crosslinking of Powdered Collagen with DMT-MP with IPP (Test 9 of Table 2)

I) Synthesis of DMT-MP

In a flask provided with magnetic stirring there were introduced 500 mg (2.85 mmol) of CDMT disslovled in 10 mL of THF to which there were added drop by drop 350 µL (2.85 mmol) of MP. After 2 h there was obtained a white precipitate that was recovered by filtration (yield of 60%).
$^1$H NMR ($D_2O$, 300 MHz, ppm) $\delta_H$: 4.42 (d, 2H), 4.06 (s, 6H), 3.54 (m, 2H), 3.32 (s, 3H), 2.0-1.4 (m, 6H); $^{13}$C NMR (D2O, 75 MHz, ppm) $\delta_c$: 174.38, 171.24, 62.44, 57.44, 21.54, 20.30; m.p. 71.0° C.

ii) In a beaker provided with magnetic stirring there were suspended 500 mg of powdered collagen in 50 mL of water. To the mixture there were then added 82.5 mg (0.3 mmol) of DMT-MP. The mixture was left under stirring for 4 h at room temperature and subsequently the solid was filtered, washed with water, and analysed by means of DSC. (Tg=87° C.)

Example 19

Tanning of Powdered Collagen with Reagent 1 ($A_1B_3C_2D_1$) and Reagent 2 ($F_7G_6H_5$), Test 10 of Table 2

The test was conducted in a way similar to what is presented in Example 10.

Formulation of Reagent 1 ($A_1B_3C_2D_1$): 0.6M solution of 2-chloro-4,6-dimethoxy-1,3,5-triazine, and of 0-6 wt % of BES, 0.5-1.0 wt % of $KClO_4$, and water.

Formulation of Reagent 2 ($F_7G_6H_5$): 0.3M solution of MP, 0.1-0.8% of Tris NaCitrate, $H_5$: SDS, and water.

Tg=83° C.-89° C. as the concentration of Reagents 1 and 2 used varies.

Example 20

Tanning of Leather with Reagent 1 ($A_1B_3C_2D_1$) and Reagent 2 ($F_7G_6H_5$)

The test was conducted in a way similar to what is presented in Example 11, where Reagent 1 and Reagent 2 are formulated in a way similar to what is presented in Example 19.

Tg=82° C.-90° C. as the concentration of Reagents 1 and 2 used varies.

Finally, it should be emphasized that, even though the present invention has been described purely by way of non-limiting illustration, according to its preferred embodiments, variations and/or modifications may be made by persons skilled in the branch, without thereby departing from the corresponding sphere of protection, as defined by the annexed claims.

The invention claimed is:

1. A method for stabilization of collagen matrices and for condensation of natural and synthetic polymers, comprising performing a single-step reaction with a pair of reagents,
   wherein a first reagent (Reagent 1) is a composition comprising:
   a) at least one or more 2-halo-4,6-dialkoxy-1,3,5-triazines of formula III:

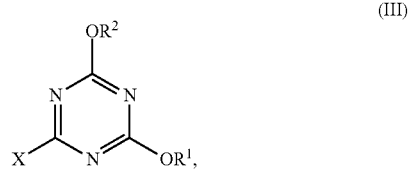

(III)

wherein:
$R^1$ and $R^2$ are independently —$CH_3$, —$CH_2CH_3$, —CH$(CH_3)_2$, —$(CH_2)_2CH_3$, or —$(CH_2)_3CH_3$; and X is Cl$^-$ or Br$^-$;
b) a buffer selected from the group consisting of MES, ACES, BES, POPSO, TRIS, HEPPSO, TAPS and Tris-NaCitrate;
c) an inorganic salt of formula $X^+Y^-$, wherein $X^+$ is selected from the group consisting of Na$^+$, K$^+$, and Ag$^+$, and $Y^-$ is selected from the group consisting of $ClO_4^-$, $BF_4^-$, and Cl$^-$; and
d) a solvent selected from the group consisting of aliphatic ether, alcohol, water, acetone and THF, and
a second reagent (Reagent 2) is a composition comprising:
a) a tertiary amine selected from the group consisting of TMA(trimethylamine), TEA (triethylamine), DEMA (diethylmethylamine), NMM(N-methylmorpholine), NEM(N-ethylmorpholine), MPD(methylpyrrolidine), and MP(methylpiperidine), and/or a quaternary salt thereof;
b) a buffer selected from the group consisting of BES, MOPS, TRIS, POPSO, TAPS and Tris-NaCitrate; and
c) a solvent selected from the group consisting of aliphatic ether, alcohol, water, acetone and THF.

2. The method according to claim 1, wherein the first reagent comprises one or more 2-halo-4,6-dialkoxy-1,3,5-triazines of formula III as an active principle, in a concentration ranging between 0.1 and 1.0 M.

3. The method according to claim 1, wherein Reagent 2 comprises one or more of the tertiary amines, and/or a quaternary salt thereof as an active principle, in a concentration ranging between 0.1 and 1.0 M.

4. The method according to claim 1, wherein Reagent 2 further comprises an additive for the buffer.

5. The method according to claim 4, wherein the additive for the buffer of Reagent 2 is selected from the group consisting of NaCl, $Na_2HPO_4$, NaOAc, KCl, SDS, glycine, boric acid, EDTA, and $NaN_3$.

6. The method according to claim 1, wherein the stabilization of collagen matrices and the condensation of natural and synthetic polymers is implemented through reactions of condensation, cross-linking, grafting and curing.

7. The method according to claim 1, wherein the natural and synthetic polymers are selected from polyacrylic acid, polyethylene, cellulose, modified cellulose, polysaccharides, starch and lignin.

8. The method according to claim 1, wherein the solvent of Reagent 1 and Reagent 2 is water.

9. The method according to claim 1, wherein the collagen matrices derive from waste of foodstuff industry.

10. The method according to claim 9, further comprising the steps of:
  a) suspending a pelt in water in a reactor;
  b) adding the first reagent and the second reagent to the reactor in a concentration ranging between 3 and 22 wt % with respect to the weight of the pelt; and
  c) removing the spent bath from the reactor and flushing the reactor with water.

11. The method according to claim 9, wherein the two reagents are added simultaneously, or in succession with the Reagent 1 followed by the Reagent 2, to the bath containing pelts in suspension.

12. The method according to claim 9, wherein the two reagents are added simultaneously to the bath containing pelts in suspension pre-stirred, at a temperature between 10° C. and 45° C.

* * * * *